United States Patent [19]
Cerwin

[11] Patent Number: 5,984,874
[45] Date of Patent: Nov. 16, 1999

[54] PRESSURE AND TEMPERATURE SENSOR TRANSDUCER ARRAY

[75] Inventor: Stephen A. Cerwin, San Antonio, Tex.

[73] Assignee: Southwest Research Institute, San Antonio, Tex.

[21] Appl. No.: 08/911,216

[22] Filed: Aug. 14, 1997

[51] Int. Cl.⁶ .................................................. A61B 5/00
[52] U.S. Cl. ...................... 600/549; 600/561; 600/503; 600/500; 600/485
[58] Field of Search .............................. 73/800; 250/525; 356/32; 600/486, 488, 545, 561

[56] References Cited

U.S. PATENT DOCUMENTS

| | | | |
|---|---|---|---|
| 4,663,656 | 5/1987 | Elabd et al. | 358/75 |
| 4,802,488 | 2/1989 | Eckerle | 128/672 |
| 5,103,831 | 4/1992 | Niwa | 128/672 |
| 5,128,535 | 7/1992 | Bock et al. | 250/227.21 |
| 5,159,323 | 10/1992 | Mase et al. | 340/712 |
| 5,277,067 | 1/1994 | Holland et al. | 73/723 |
| 5,309,767 | 5/1994 | Parmar et al. | 73/705 |

*Primary Examiner*—Robert L. Nasser
*Attorney, Agent, or Firm*—Kammer & Huff, PLLC

[57] ABSTRACT

A pressure or temperature sensor array utilizing a combination of liquid crystal material and charge coupled device (CCD) sensor array. The device generally comprises a liquid crystal material enclosed in a planar capsule, one side of which has a flexible outer membrane which is placed on the surface whose pressure and/or temperature is to be measured; a light source used to illuminate the liquid crystal material; and a charge coupled device (CCD) array which detects the variations in the optical signature of the liquid crystal material due to changes in pressure or temperature. The device may further include an optical waveguide for controlling transmission of light from the light source to the liquid crystal material.

10 Claims, 2 Drawing Sheets

PRESSURE AND TEMPERATURE SENSOR TRANSDUCER ARRAY

BACKGROUND OF THE INVENTION

1. Field of the Invention

The present invention relates generally to pressure and temperature measurement devices. The present invention relates more specifically to the use of liquid crystal materials and charge coupled device technologies in combination for the measurement and monitoring of small pressure and temperature variations with a high degree of topographic resolution.

2. Description of the Related Art

A problem well known in the medical field is the need to quickly and accurately ascertain a patient's blood pressure and temperature. This may be required infrequently in conjunction with a physical or routine check-up or may need to be constant as when monitoring patients with prolonged illnesses such as high blood pressure and/or unstable temperatures.

Some blood pressure monitoring devices have been created to provide constant information regarding blood pressure with the least amount of inconvenience to the patient. Such systems typically are worn around the wrist and attempt to apply an array of pressure sensing elements with constant pressure over an artery. These systems principally select one pressure sensing element from the array from which to calculate the blood pressure in the artery. U.S. Pat. Nos. 4,269,193 and 4,802,488, both by Eckerle, describe various methods of optimizing the selection of the single pressure element from which the blood pressure will be measured. In the Eckerle patents information about the patient's physical characteristics is input into the device and used to estimate the diameter of the underlying artery. Then, based on diastolic and systolic pressure and pulse amplitude values, the device selects a pressure-sensing element calculated to be near the center of the artery from which the blood pressure is monitored. A drawback of this device and others like it, is that a single pressure-sensing element is used as the basis for all blood pressure measurements.

Other pressure-sensing devices have been developed which increase the number of individual pressure-sensing elements contacting the area to be measured. U.S. Pat. No. 5,277,067, issued to Holland et al., uses standard integrated circuit fabrication techniques to create an array of pressure sensor elements. The fabrication process includes forming a hole in an insulating layer deposited on an electrical cathode layer, depositing material to form an electrical cathode tip into the hole, and bonding an electrical anode layer onto the insulating layer so as to be slightly separated from the cathode tip. Each pressure sensor element detects changes in pressure due to variations in the initial separation between the anode layer and the cathode tip based on the electric current produced by tunneling or electron field emission.

Other pressure-sensing devices have been constructed which make use of the optical properties of crystal materials to detect variations in pressure. One such device is described in U.S. Pat. No. 5,309,767, issued to Parmar et al. The device described by Parmar consists of a liquid crystal material placed between two transparent, electrically conductive films which are biased by a voltage. The bias voltage creates an electric field that results in an initial state of orientation of the liquid crystal material. Subsequent application of pressure to one of the flexible films results in a change in the electric field and a corresponding change in the orientation of the liquid crystal. The intensity of polarized light directed into the liquid crystal and detected by an analyzer changes as a function of the applied pressure and provide a means of measuring the pressure variations. While the liquid crystal material is grouped into minute pockets within the pressure sensor, the device measures the cumulative change in pressure rather than being able to detect the specific change in pressure experienced by each pocket.

Such prior art pressure-sensing devices, as previously described, suffer from certain inherent problems. Typically, they are unable to detect small variations in pressure at a number of points simultaneously and, therefore, lack high spatial or topographic resolution. In addition, none of the prior art devices combine liquid crystal based pressure or temperature sensors with high resolution charge coupled devices to provide a full solid state array.

SUMMARY OF THE INVENTION

It is therefore an object of this invention to provide a new type of pressure and temperature sensor.

It is another object of the present invention to provide a compact device for measuring small variations in pressure or temperature.

It is a further object of the present invention to provide a pressure and temperature sensing device with high spatial or topographic resolution.

It is another object of the present invention to provide an accurate, non-invasive blood pressure detector.

It is a further object of this invention to provide a pressure and temperature sensor employing an array of charge coupled devices (CCD) operable in conjunction with the optical properties of a liquid crystal material.

According to the present invention, the foregoing and other objects and advantages are attained by a pressure sensor array utilizing a combination of liquid crystal material and charge coupled device (CCD) technologies. The device generally comprises a liquid crystal material enclosed in a planar capsule, one side of which has a flexible outer membrane which is placed on the surface whose pressure and/or temperature is to be measured; a light source used to illuminate the liquid crystal material; and a CCD array capable of detecting the variations in the optical signature of the liquid crystal material due to changes in pressure and/or temperature. The device may further include an optical waveguide for controlling the transmission of light from the light source-to the liquid crystal material while minimizing direct illumination of the CCD array. Localized changes in the optical properties of the liquid crystal material respond to pressure changes across the area being measured and are detected by the CCD array.

Additional objects, advantages and novel features of the invention will be set forth in part in the description which follows, and in part will become apparent to those skilled in the art upon examination of the following, or may be learned by practice of the invention. The objects and advantages of the invention may be realized and attained by means of the instrumentalities and combinations particularly pointed out in the appended claims. Still other objects and advantages of the present invention will become readily apparent to those skilled in this art from the following detailed description, wherein multiple preferred embodiments of the invention are shown and described, simply by way of illustration of the best mode contemplated by the inventor for carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

DESCRIPTION OF THE PREFERRED EMBODIMENT

As generally described above, the device of the present invention has practical application in a number of situations. The device may be used to monitor pressure and temperature with a high degree of spatial resolution over the surface area being measured. The invention described may be used by medical personnel to ascertain blood pressure or skin temperature in most medical situations in which access to the patient's skin is available. In addition, the device may be used by patients, such as those having a history of high blood pressure, to consistently and accurately monitor themselves for early detection of abnormal readings. The device may also be used outside the hospital area, in facilities such as nursing homes and extended care facilities. The device is not limited to institutional use, but also has practical application for in-home health care and blood pressure or temperature monitoring for the increasing number of patients who choose to have medical care provided in their own homes.

The device also has broader application to the measurement and characterization of pressure or temperature outside the medical field, such as in manufacturing processes where variations in temperature or pressure over a small area must be measured with a high degree of resolution. In short, the device has application whenever a dense array of pressure or temperature transducers might be required.

Figure 1:
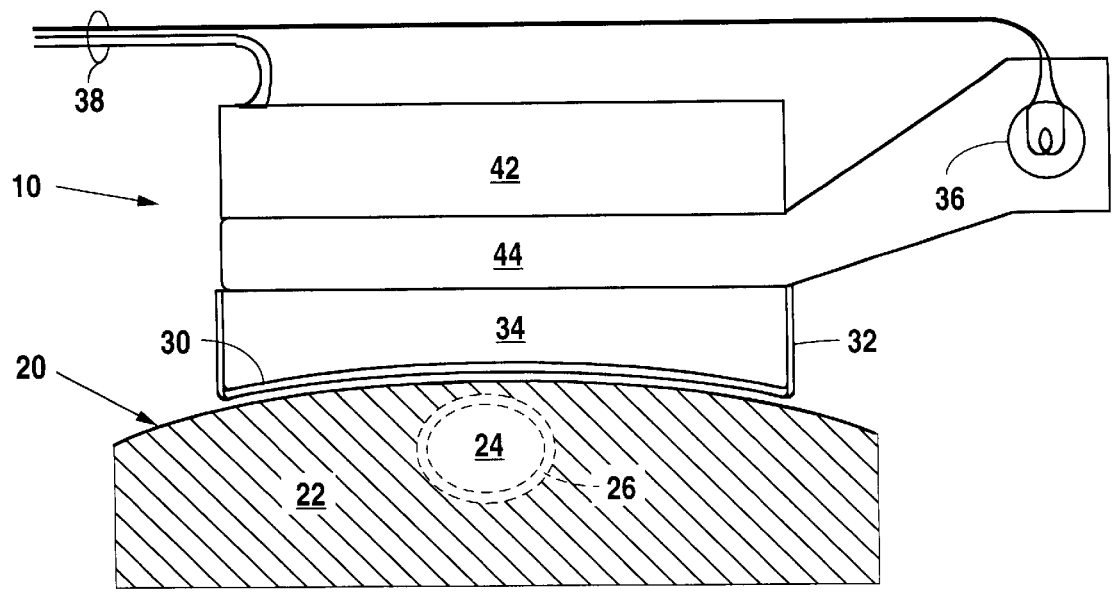
FIG. 1 is a schematic diagram of a preferred embodiment of the present invention shown as it might be applied in position over a human artery from which blood pressure may be measured.

Reference is made, therefore, to FIG. 1 for a description of a first embodiment and a first application of the current invention. FIG. 1 shows a schematic diagram of a preferred embodiment of the present invention configured for use as a blood pressure monitoring device. In this embodiment, the device (10) is shown positioned adjacent the surface (20) of the skin (22) of the subject whose blood pressure is to be monitored. The device (10) contacts the surface (20) of the subject's skin (22) at a point where an underlying artery (24) having an arterial wall (26) lies relatively close to the surface (20) of the skin (22) so as to allow a blood pressure measurement to be taken. The device (10) is held next to the skin (22) with fairly constant pressure in order to profile the pressure distribution across the underlying artery (24). As shown in FIG. 1, the pressure of the device (10) on the subject's skin (22) may cause a slight flattening of the arterial wall (26) on the side of the artery (24) closest to the surface (20) of the skin (22), although such arterial wall flattening is not required for an accurate blood pressure measurement.

The device (10) contacts the skin (22) of the patient whose blood is to be monitored at its surface (20) as described above. In the preferred embodiment, a flexible outer membrane (30) makes direct contact with the surface (20) of the patient's skin (22). The flexible outer membrane (30) serves as the bottom wall of a capsule (32) which contains a liquid crystal material (34). In a preferred embodiment, the capsule (32) has a general shape of a rectangular solid. The bottom wall of the capsule (32) is the flexible outer membrane (30), whereas the sides and top of the capsule (32) need not be flexible. The function of the flexible outer membrane (30) is to allow pressure impulses from the artery (24) to pass through the membrane (30), causing localized deformations in the liquid crystal material (34). The deformations in the liquid crystal material (34) cause corresponding modulations in the optical properties of the liquid crystal material (34) immediately around the areas producing the deformations. These changes in optical properties can then be monitored and interpreted as blood pressure information for the artery (24) by the device (10). Different liquid crystal materials (34) may be chosen depending on their respective optical properties in response to the deformations caused by the changes in pressure. The optical properties of any one liquid crystal material (34) chosen to be used in the device (10) must also take into account the chromatic content of the light source which illuminates the liquid crystal material (34) for optimal operation of the device (10).

The next element in the pressure sensor device (10) is waveguide (44) which is coupled to the external light source (36). In the preferred embodiment, the waveguide (44) is a planar optical waveguide which is connected to the top of capsule (32). The waveguide (44) serves to enhance illumination of the liquid crystal material (34) while minimizing direct illumination of the CCD (charge coupled device) sensor array (42), described in more detail below. Thus, the waveguide (44) is a middle layer of the device (10) between capsule (32) and the CCD sensor array (42). The top of the capsule (32) must be transparent to the light emitted by the light source (36) in order for the light to properly interrogate the liquid crystal material (34).

Any of a number of waveguide devices employing a variety of methods to control the task of transmitting light from the light source (36) to the liquid crystal material (34) may be used. For example, the waveguide (44) may operate to control the angle of incidence of the light emitted from the light source (36). Alternatively, the waveguide (44) may consist of non-parallel faces creating a wedge shape which favors optical propagation in a preferred direction, or the waveguide may achieve a preferential illumination direction by controlling the refractive indices at the interfaces between the waveguide (44) and both the liquid crystal material (34) and the sensor array (42). The waveguide (44) might also make use of partially reflective coatings or diffractive gratings to control illumination. Finally, the waveguide (44) may include fiber optic elements to directly control light propagation from the light source (36). For certain applications, a combination of two or more of these methods may prove useful.

In yet another preferred embodiment, the device may not contain a waveguide (44), but may instead have the optical sensor array (42) placed directly on top of the capsule (32) housing the liquid crystal material (34). Light needed for proper operation of the device (10) is then injected directly into the skin adjacent the periphery of the device (10). The injected light will then diffuse into the flesh and illuminate the liquid crystal material (34) from below by back scatter.

The next element in the pressure sensor device (10) is the optical sensor array (42) which detects and translates the variations in optical signature from the illuminated liquid crystal material (34) due to variations in pressure or temperature. The optical sensor array (42) is located adjacent to and above the waveguide (44) if a waveguide (44) is used, and is otherwise placed adjacent and on top of the capsule (32) when no waveguide is used. In the preferred embodiment, the optical sensor array (42) is a CCD (charge coupled device) array. The use of a CCD sensor array (42) has the advantage of extremely high spatial resolution over the area being measured. For the blood pressure sensor application, a modern ½ inch CCD array (of the type used in high resolution cameras) has 768×494 picture elements, or 379,392 pixels in an area 0.5-inch×0.32-inch. Because CCD arrays are typically used in conjunction with video cameras, facsimiles and the like, data acquisition by the array (42) is at video rates, or 60 frames per second (30 frames per second with interleaved scanning). The CCD array (42) also has the advantage of being operable from a modest electrical source, such as a battery (not shown).

For each pixel element of the CCD array (42), a number corresponding to the intensity and/or color of the light detected at that pixel is produced as output data. Time variable data output from the CCD array (42) may then be stored in a register for later analysis, or may be analyzed by an on-board micro processor (not shown). In the blood pressure application described herein, the output data is used with well known formula for calculating the blood pressure within the artery (24) based on the pressure changes sensed by the device (10).

Many CCD imaging arrays (42) are available from which to choose for applications such as described herein. Such CCD devices are typically operable at modest voltage (e.g., 5–9 volts DC) and current levels. The output signal from the CCD array (42) is typically in standard video format, i.e. horizontal scan lines are read out sequentially from top to bottom, separated by horizontal sync pulses. Data from the CCD array (42) may be displayed directly as image data on a remote video monitor, or the data may be analyzed by additional signal processing circuitry such as a microprocessor to produce either a real time blood pressure value, as described above, or a time variable pressure topography.

Figure 2:
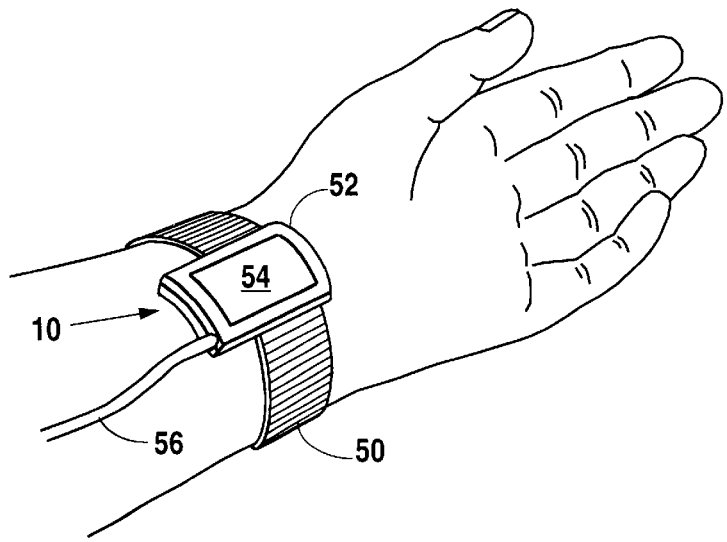
FIG. 2 is a pperspective view of the preferred embodiment of the present invention as applied in FIG. 1 showing a typical positioning of the device on a human wrist for providing a continuous external measurement of blood pressure.

FIG. 2 shows one possible implementation of a monitoring device (52) for tracking blood pressure or skin temperature of the wearer. As is shown, the monitor (52) is strapped to the user's wrist with a band (50) at the location to be monitored. The band (50) provides almost constant pressure between the device and the wearer's skin. The pressure or temperature monitoring device (10) is located immediately adjacent the wearer's skin inside the monitor (52) and functions as herein previously described. Above the pressure or temperature monitor device (10) may be located the face of the monitor (52) which houses a display (54) for showing the user the pertinent blood pressure or temperature information. In this embodiment, the circuitry for calculating the blood pressure or temperature and for operating the display (54) is contained within the monitor (52). Alternatively, monitor (52) could incorporate a signal connection (56) for relaying the information translated by the CCD array within monitor (52) to a remote location where it might either be displayed or stored for later data retrieval. In either case, all of the device components necessary for acquiring and translating either pressure or temperature information into a retrievable signal is provided within the monitor unit (52).

Figure 3:
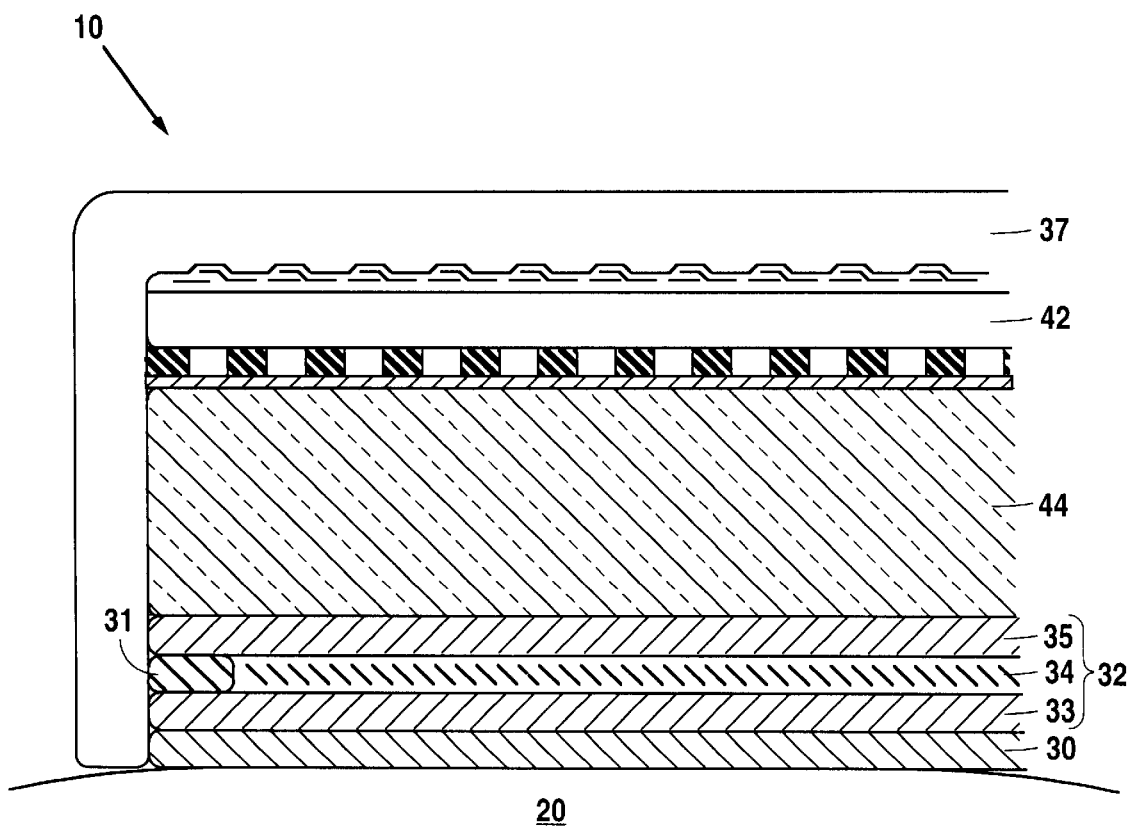
FIG. 3 is a detailed cross-sectional diagram of a preferred embodiment of the present invention disclosing the various component layers of the device.

Reference is now made to FIG. 3 for a detailed description of a typical cross-section of the layers of the element components of the present invention. Describing in more specific detail the structure of the device shown in FIG. 1, FIG. 3 discloses the relative positioning and the various layered contacts between the component elements of the present invention. Device (10) is shown in FIG. 3 as it might be placed adjacent to skin surface (20) for a patient whose blood is to be monitored. In direct contact with skin surface (20) is flexible outer membrane (30) which serves to communicate changes in the skin surface (20) brought about by pressure changes under the influence of the flow of blood within the artery beneath the skin surface (20). These pressure changes are transmitted to liquid crystal capsule (32) comprised of capsule wall layers (33) and (35) which are separated and positioned by spacer (31). Within the void formed between capsule walls (33) and (35) is positioned liquid crystal material (34).

Immediately above and adjacent the transparent wall (35) of liquid crystal capsule (32) is light waveguide (44). Waveguide (44) is any of a number of different types of light conductors suitable for directing light to and illuminating the liquid crystals within liquid crystal capsule (32). Characteristics of waveguide (44) are such that light is directed onto liquid crystal material (34) but not up into CCD sensor array (42).

CCD sensor array (42) is positioned directly above waveguide (44) parallel to LCD capsule (32) in a manner that permits access by CCD sensor array (42) to reflected light (or transmitted light in some embodiments) from liquid crystal capsule (32). Each specific portion of liquid crystal material (34) is interrogated and identified by one element in CCD sensor array (42).

The entire set of elements layered as indicated in FIG. 3 is enclosed in a non-flexible, non-transparent enclosure wall (37) which serves to maintain the relative positions of the component layers as described and to prevent the unintended interference of extraneous light or pressures into the device.

The basic structure shown in FIG. 3 is appropriate not only for pressure and temperature applications in the medical field, but the same basic configuration is appropriate for application in a number of different fields where slight variations in temperature and pressure across a surface area need to be monitored.

As mentioned above, the device (10) may be used to measure localized temperature changes with a high degree of resolution as well. The operation of the device (10) when functioning as a temperature indicator is quite similar to that described above for functioning as a pressure sensor. Specifically, localized changes in the temperature across a surface monitored by the device (10) cause corresponding changes in the optical properties of the liquid crystal material (34) positioned adjacent the area being monitored. Just as for the pressure sensor, the specific optical responses of the liquid crystal material (34) to variations in temperature dictate the chromatic content of the light source (36). For example, liquid crystal materials exhibiting color variations in response to pressure or temperature changes indicate the use of a white light source and a CCD (charge coupled device) sensor array (42) sensitive to color. Alternatively, if the liquid crystal material modulates the amplitude of light passing through it in response to pressure or temperature variations, a monochromatic light source, such as a light emitting diode will be the preferred illumination source.

In addition to monitoring blood pressure and body temperature of living animals, the device (10) has other applications as well. The sensor has a wide range of applications in the industrial fields whenever a high degree of resolution involving pressure or temperature is required. The device may be used to measure air pressure on a membrane or for measuring temperatures and pressures within containment vessels and the like. In some manufacturing processes where strict pressure and temperature requirements exist, devices of the present invention could be implemented in a number of locations in the process to maintain and record these precise temperature and pressure requirements. In general, the present invention provides a useful method for characterizing pressure variations on a flexible surface and temperature variations on a flexible or rigid surface. In either case, it is possible to use the device of the present invention to detect and identify very fine variations in temperature or pressure across a small section of surface area. A large number of different processing mechanisms can be implemented in association with the present invention to provide real time pressure and temperature data, and the control of various processes dependent upon pressure or temperature values.

In addition, it is anticipated that the same displacements that reflect pressure changes sensed by the device of the present invention might likewise indicate variations in other mechanical features of the surface or substance being monitored. In other words, physical movement of the surface which might result from vibrations, sound waves and the like present within the material would also create variations in the optical characteristics of the liquid crystal material held in contact with the surface. These variations could also be detected, identified, and quantified by the system of the present invention. Such uses of the device could help in monitoring vibrations, stresses, and fatigue characteristics of materials in a variety of industries.

It is intended that the above descriptions of preferred embodiments of the structure of the present invention and the description of its potential applications are but two enabling best mode embodiments for implementing the invention. Other applications are likely to be conceived of by those skilled in the art, which applications still fall within the breadth and scope of the disclosure of the present invention. The primary importance of the present invention lies in its use of optics in combination with a CCD array to provide a compact, yet highly accurate pressure and/or temperature sensor with high resolution. Its benefits derive from the versatility of application of the present invention and its low cost and accuracy. Again, it is understood that other applications of the present invention will be apparent to those skilled in the art upon a reading of the preferred embodiments and a consideration of the appended claims and drawings.

I claim:

1. An apparatus for measuring pressure or temperature over a surface area, comprising:

a liquid crystal material enclosed in a planar capsule having a flexible outer membrane, said liquid crystal material having an optical signature responsive to variations in pressure or temperature over said surface area, said optical signature comprising color and amplitude variations in said liquid crystal material; and a color sensitive charge coupled device sensor array capable of detecting and mapping said optical signature of said liquid crystal material due to said variations in pressure or temperature.

2. The apparatus of claim 1, further comprising a light source for illuminating said liquid crystal material.

3. The apparatus of claim 2, wherein said light source is external to said liquid crystal material and said sensor array, and said apparatus further comprises a light waveguide, said light waveguide positioned to direct light from said external light source to said liquid crystal material.

4. The apparatus of claim 1, wherein said apparatus is used to measure and record blood pressure through contact between said flexible outer membrane of said liquid crystal material and an area of skin over an adjacent blood vessel.

5. An apparatus for measuring pressure or temperature over a surface area, comprising:

a liquid crystal material enclosed in a planar capsule and having an optical signature, said optical signature comprising color and amplitude variations in said liquid crystal material, said planar capsule having at least one flexible outer membrane for placement on said surface area;

a polychromatic light source used to illuminate said optical signature of said liquid crystal material, said optical signature representative of variations in pressure and temperature on said surface area; and a color sensitive charge coupled device sensor array capable of detecting and mapping said optical signature representative of said variations in pressure or temperature.

6. The apparatus of claim 5, wherein said light source is external to said liquid crystal material and said sensor array, and said apparatus further comprises a waveguide coupled to said external light source, said waveguide operating to enhance illumination of said liquid crystal material while minimizing direct illumination of said charge coupled device sensor array.

7. The apparatus of claim 6, wherein said waveguide is located between said liquid crystal material and said CCD array.

8. The apparatus of claim 6, wherein said waveguide further comprises a plurality of non-parallel faces forming a wedge shape favoring optical propagation toward said liquid crystal material.

9. The apparatus of claim 6, wherein said waveguide uses the refractive indices at an interface of said waveguide with said planar capsule and said CCD array to achieve a preferential illumination of said liquid crystal material.

10. The apparatus of claim 6, wherein said waveguide further comprises partially reflective coatings to achieve a desired illumination of said liquid crystal material.

* * * * *